United States Patent
O'Sullivan et al.

[11] Patent Number: 5,494,043
[45] Date of Patent: Feb. 27, 1996

[54] ARTERIAL SENSOR

[75] Inventors: Martin O'Sullivan, Mountain View; Lawrence W. Brendlen, Jr., Sunnyvale; Donald Q. Dong, San Jose; Jeffrey M. Moser, Oakland; Kenneth H. Mollenauer, Santa Clara; Kenneth C. Kitlas, Fremont; William J. Kaspari, Portola Valley, all of Calif.

[73] Assignee: Vital Insite, Inc., Calif.

[21] Appl. No.: 59,425

[22] Filed: May 4, 1993

[51] Int. Cl.$^6$ .................................................. A61B 5/024
[52] U.S. Cl. .................................................. 128/687
[58] Field of Search ........................... 128/672, 687–690, 128/774, 782

[56] References Cited

U.S. PATENT DOCUMENTS

| | | | |
|---|---|---|---|
| Re. 32,180 | 6/1986 | Lewiner et al. | 128/782 X |
| 4,181,134 | 1/1980 | Mason et al. | 128/690 X |
| 4,295,471 | 10/1981 | Kaspari . | |
| 4,307,728 | 12/1981 | Walton | 128/687 |
| 4,409,983 | 10/1983 | Albert | 128/690 |
| 4,443,730 | 4/1984 | Kitamura et al. | 310/330 |
| 4,784,152 | 11/1988 | Shinoda et al. | 128/690 |
| 4,924,871 | 5/1990 | Honeyager | 128/687 X |
| 5,101,829 | 4/1992 | Fujikawa et al. | 128/687 X |

FOREIGN PATENT DOCUMENTS

| | | | |
|---|---|---|---|
| 4097738 | 3/1992 | Japan | 128/687 |

*Primary Examiner*—Angela D. Sykes
*Attorney, Agent, or Firm*—Flehr, Hohbach, Test, Albritton & Herbert

[57] ABSTRACT

A sensor that utilizes strips of piezoelectric material to noninvasively measure the surface force/displacement resulting from a blood pressure wave traveling through an artery and transmitted through the arterial wall and overlying tissue, while canceling noise artifact signals is disclosed. Piezoelectric elements create an electrical signal when pressure is applied to their surface. In the preferred embodiment, the sensor is constructed so that there are three sensing elements—a signal sensing element in the center and one noise sensing element on each side of the center element. The center element is placed over an individuals artery, e.g., the radial artery in a persons wrist. When positioned this way, the two noise sensing elements are positioned on each side of the artery.

The center element generates a signal that is a function of the pressure wave in the artery, whereas this signal is highly attenuated in the noise sensing elements. However, all three elements detect the noise artifact signals in the general area of the sensor. The area of the noise elements, when combined, is equal to that of the center element. This provides an average of the noise detected by the center element.

The signals from the two noise sensing elements are subtracted from the center element signal, thereby canceling the noise in the center element.

Also disclosed is a unique method that allows repositioning of the sensor after it has been attached to the patient, a mechanism for maintaining the appropriate hold down pressure, a wrist stabilization device for stabilizing the wrist during monitoring of the blood pressure. The present invention also allows blood pressure calibrations to be obtained using the wrist and arm stabilizer assembly.

22 Claims, 10 Drawing Sheets

ARTERIAL SENSOR

FIELD OF THE INVENTION

This invention relates generally to a noninvasive method of continuously measuring an arterial pulse for use in monitoring arterial blood pressure and/or pulse amplitude, and more particularly to a disposable sensor and sensor attachment apparatus to be used for the measurement of the surface force/displacement resulting from a blood pressure wave traveling through an artery and transmitted through the arterial wall and overlying tissue.

BACKGROUND AND PRIOR ART

An accurate measurement of the pulsatile blood pressure in a person's cardiovascular system is a necessary component in most medical procedures. An individual's blood pressure can be represented in the form of an arterial waveform representing the instantaneous pressure continuously. Normally such a waveform can only be accurately measured with an intraarterial catheter and pressure transducer. The catheter can continuously monitor blood pressure, but suffers from the obvious drawback of requiring surgical intervention and associated risks of complications.

Many devices allow blood pressure to be measured by sphygmomanometer systems that utilize an inflatable cuff applied to a person's arm. The cuff is inflated to a pressure level high enough to completely occlude a major artery. When air is slowly released from the cuff, blood pressure can be estimated by detecting well-known "Korotkoff" sounds using a stethoscope or other detection means placed over the artery. A major drawback with these devices is that they can only provide an intermittent measure of blood pressure; and they do not provide a continuous arterial pressure waveform.

Some relatively recent inventions have made possible noninvasive methods of monitoring blood pressure. Some of these devices are also capable of detecting the arterial waveform. One such method is presented in U.S. Pat. No. 4,295,471 issued to William J. Kaspari. This patent discloses a sensor which uses two piezoelectric elements placed in a housing, and facing opposite directions. These piezoelements are acoustically and electrically isolated from each other. The sensor is placed in a pocket at the distal end of an inflatable cuff, which is then wrapped around a person's arm. The device disclosed in the '471 patent monitors the Korotkoff sounds as the pressure in the inflatable cuff is increased to a level just greater than that necessary to occlude the artery. One piezoelectric sensor element is placed directly over the artery and detects the Korotkoff frequencies, as well as motion artifact signals produced by muscle movement and/or other external factors. The second sensor element is placed directly against the air bag. Because the air bag highly attenuates the Korotkoff frequencies, the second sensor essentially only detects an artifact signal, which is substantially equivalent to the artifact portion of the signal detected by the first sensor element. The signal from the second sensor element is subtracted from the signal from the first sensor element, providing an arterial waveform with reduced common-mode artifact.

The '471 patent teaches detecting the arterial waveform in a noninvasive manner that mitigates artifactual contamination of the signal of interest. However, the device disclosed in the '471 patent is not intended to be disposable, and does not lend itself to application at body sites such as the radial artery, and generally requires a pressure cuff applied over the sensor. All other devices which externally measure the arterial waveform also suffer from the common problem of including a large artifact signal along with the arterial signal.

SUMMARY OF THE INVENTION

The present invention seeks to overcome the problems associated with the prior art by not only reducing the effects of artifact on the measured arterial pulse signal, but also by providing a means to properly apply and maintain the sensor over a person's artery, thus providing a more accurate, repeatable, and complete waveform representing a person's arterial pulse.

In the present invention, a strip of piezoelectric material is utilized to detect the pressure wave in an artery from the body surface. Piezoelectric elements create an electrical signal when a displacement force is applied to them. The piezoelectric sensor is placed on the skin over a person's artery, and measures the intra-arterial pressure wave through the arterial wall, overlying tissue, and skin. The varying force generated by the pulsatile blood pressure within the artery causes the piezoelectric strip to experience a pulsatile tensioning, and to generate a charge proportional to this tension. The piezoelectric strip acts as a charge source, and a conventional charge amplifier can be used to amplify the charge signal and yield a voltage waveform proportional to the charge. However, muscle movement in the arm (or other body part) on which the piezoelectric sensor is placed adds motion artifact to the pressure wave signal. Additionally, artifactual signals are generated from other sources such as vibration, external bumping of the patient, etc. It is desirable to attenuate these artifacts in the signal. A preferred embodiment of the invention includes 3 elements—a center element and 2 smaller elements on each side of the center element. The center element is placed directly over the artery. The smaller side elements are positioned off the sites directly over the artery, and are minimally sensitive to the pressure wave signal from the artery; but because of their proximity to the center element they have substantially the same sensitivity to the artifact signal as the center piezoelectric strip that is positioned over the artery. The side elements essentially average the artifact signals measured on each side of the pulse site in order to more closely approximate the artifact at the pulse site. To do this the total charge-generating area of the 2 side elements are the same as that of the center element. The signal from the sum of the 2 side elements contains substantially the same noise or artifact as the center element but contains minimal arterial signal. The signals from the side elements are subtracted from the signal from the center element to substantially cancel the noise or artifact, while maintaining the arterial signal.

The basic piezoelectric material is a polymer film, typically specially processed polyvinylidene fluoride (PVDF) that exhibits the property of creating an electrical charge when tension is applied to the film. The term "piezofilm" will be used to indicate piezoelectric film.

In the preferred embodiment, a single strip of piezofilm is used to form the sensing elements. A support mechanism creates three parallel channels that are bridged by the single piezofilm strip. The strip is securely attached to the edge of each channel and is thus divided into three distinct portions forming the 3 sensing elements. The center element is formed from the center of the piezofilm, and is typically long enough to span the artery. The remaining two portions form the side elements that are used to measure the signal while sensing only minimal arterial pulse signal. The piezofilm strip dimensions are such that it is easily deflected by each pulsation of the artery, and accurately reproduces the frequency components of the pressure waveform as measured on the skin surface. An area of the film that lies within each of these three channels, on the side of the film away from the skin, is coated with a silver filled ink to form an electrode for each element. The opposite side of the film (the side that contacts the skin), is also coated with the same material to form the second electrode for each of the elements. The skin-side contact is common to all elements, thereby removing any unwanted (common-mode) electrical signals picked up from the patients skin, such as electromagnetic interference.

The individual element within each channel is coated with an insulating material following application of the conductive coating to prevent electrical shorting of these elements due to moisture or other conductive material.

In the preferred embodiment, the signals from each element are amplified by a separate charge amplifier, and electronic means are provided to process these signals to provide other signals used for correctly positioning the sensor over the artery. In an alternate embodiment, 2 strips of piezofilm are used to form the noise-canceling subtraction of the outside elements signals from the center element signal. This yields a single signal to amplify, and precludes generation of the signals for positioning.

In order to accurately detect the pressure waveform, and to maintain detection of the waveform in an undistorted manner, the sensor must be appropriately applied to the site to be monitored. In addition, an appropriate hold-down pressure which is an external force applied to the sensor to hold it securely in position, must be determined and maintained. To optimize the signal and artifact pick-up in each of the elements of the sensor, it is desirable to provide uniform coupling between each element and the site to which it is applied. The hold-down mechanism is designed to provide substantially uniform pressures on the elements, perpendicular to the surface of the skin.

Since the site initially chosen for application of the sensor is the radial artery, the sensor is designed to easily access the artery without requiring excessive pressure. Excessive pressure may partially or completely occlude the artery. Furthermore, once the required access is achieved, it is necessary to maintain the sensor in position.

In one embodiment of the three element sensor, each of the two noise elements is mounted on an independent frame and is attached to the center element in such a way that each of the outer segments is free to seek its own angle with respect to the center segment to conform to the contour of each individual wrist. The frame is attached to the frame adjacent to it by means of a hinge. Hinge material can be a thin flexible plastic, a suitable adhesive backed tape, a hinge molded into the frame structure, or other means. The piezofilm is attached to the frame using suitable means.

To apply the appropriate hold-down pressure, an inflatable air compartment or bubble is placed between the sensor frame opposite the film side and a backing plate assembly that is attached directly or indirectly to the side of the wrist opposite the sensor site to yield a sensor hold-down mechanism. The inflation of the bubble forces the elements to conform to the patient's wrist, while maintaining uniform and constant hold down forces on the elements substantially perpendicular to the skin.

The site being monitored (e.g., the radial artery) is maintained in a fixed position in order to minimize artifact and to maintain sensor positioning. More specifically, wrist rotation and finger flexing is restricted. Means for maintaining the proper wrist position is described.

Another feature of the present invention is that it can contain a means of obtaining calibration and/or verification measurements of blood pressure via an occlusive cuff that is built into the wrist stabilization device, and can also utilize the disposable noise-canceling sensor for detection of the Korotkoff sounds.

DETAILED DESCRIPTION OF THE PREFERRED AND ALTERNATIVE EMBODIMENTS

Figure 1A:
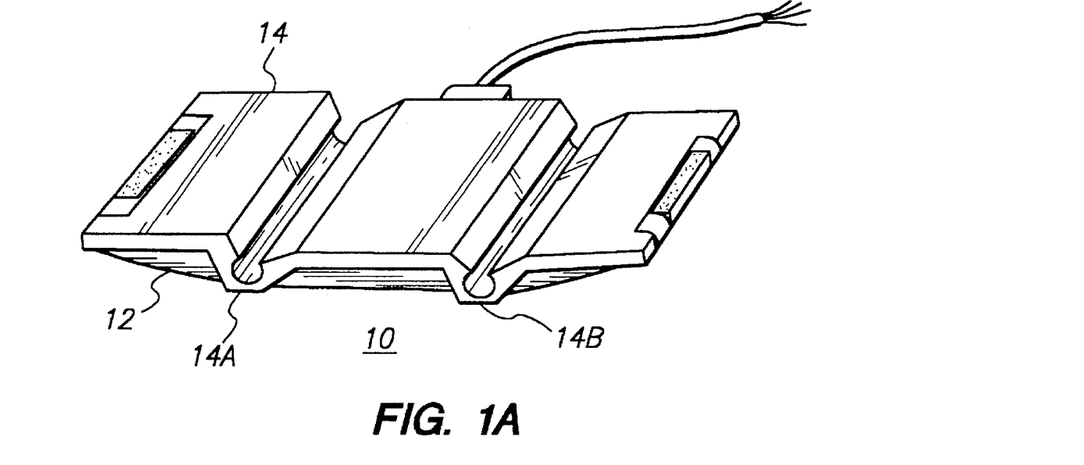
FIG. 1A is a perspective view of a preferred embodiment of the arterial sensor of the present invention.
Figure 1B:
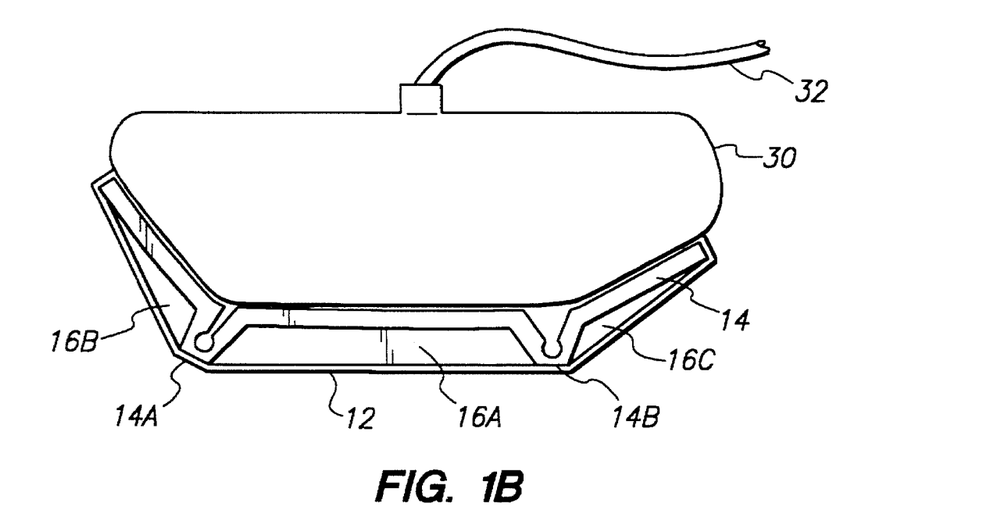
FIG. 1B is a side view of the embodiment shown in FIG. 1A, showing the sensor in a flexed position with an air bubble inflated.
Figure 1C:
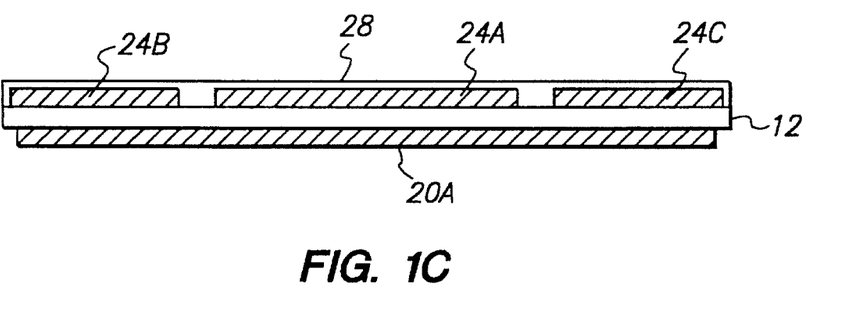
FIG. 1C is an edge view of the piezoelectric film shown in FIG. 1A and 1B.

FIG. 1A shows a perspective view of the preferred embodiment of a sensor 10 according to the present invention. The sensor 10 consists of a strip of piezoelectric material 12 which is used to measure the force or displacement resulting from a pressure wave created as blood is forced through an artery. The piezofilm strip 12 is attached to support member 14, which forms a center channel 16A and two outer channels 16B and 16C as shown in FIG. 1B. The support member 14 may be constructed of rigid plastic or similar material and its primary purposes are to create the channels 16 (A–C) which are bridged by piezofilm strip 12 and to isolate the forces on each of the three sensing elements. In creating three channels 16 (A–C), the support member 14 segments the piezofilm strip 12 into three sections 18 (A–C) respectively shown in FIG. 1E, a center section and two outer sections, which are the three sensing elements. The piezofilm is attached to the edges of each channel by, for example, glue, and is aligned perpendicular to the channels, such that tensions developed in the film are developed along its axis of greatest sensitivity.

In the preferred embodiment, support member 14 contains two rails (14A and 14B), which define the center channel. These rails serve to provide means of attaching film 12, thereby creating the three independent sensing regions, and these rails contain a groove that forms a hinge that permits each of the outside elements to flex with respect to the center element. They therefore act as "living" hinges, and provide the capability of the sensor to conform to various shapes. Additional rails can be provided at each end of the support member 14 for added film-attachment area and may prevent the film from touching the base of the member when excessive force is applied to the film.

Figure 1D:
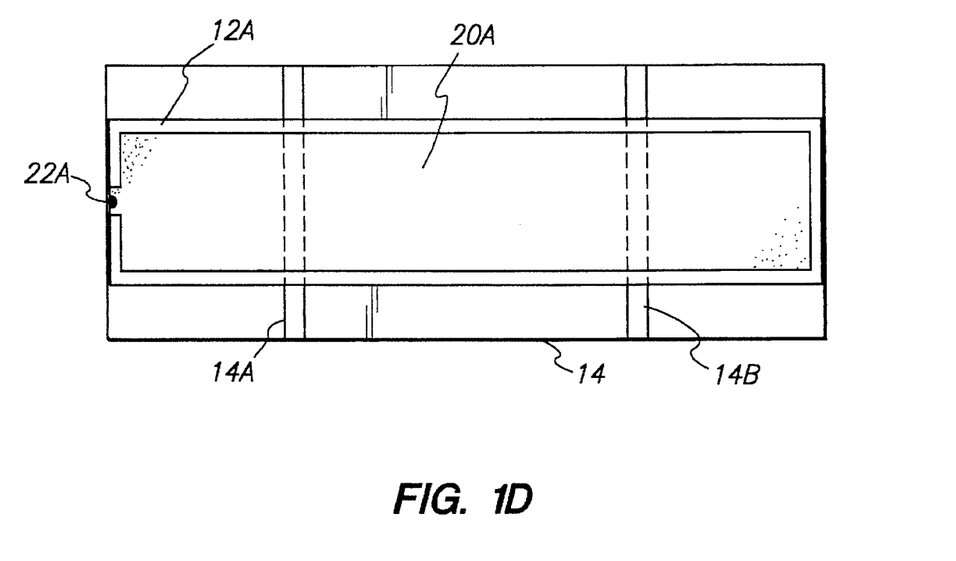
FIGS. 1D and 1E are bottom and top views, respectively, showing the piezoelectric film and conductive coatings.
Figure 1E:
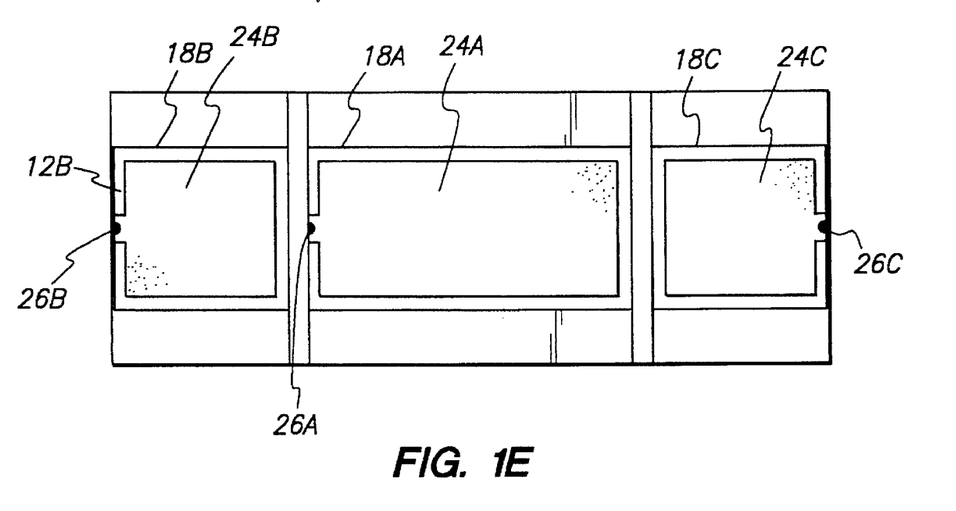

The width and thickness of piezofilm strip 12 are also relevant to the strip's ability to detect and accurately reproduce the arterial waveform. Specifically, dimensions are selected so as to accurately reproduce all of the frequency components contained in the blood pressure waveform over a wide range of blood flow velocities, while also producing a sufficiently large charge output. In the preferred embodiment, the strip 12 on the bottom of the sensor (facing the skin) has the approximate dimension of 5 mm×20 mm with the sections 18B and 18C each being 5 mm×5 mm and section 18A being 5 mm×10 mm. As shown in FIGS. 1D and 1E, the piezofilm strip 12 has two sides: first side 12A, which faces outward from the sensor 10 and is positioned against the tissue of a patient, and a second side 12B, which faces the channels 16A, 16B and 16C. A first conductive coating 20A is applied to the first side 12A of the piezofilm strip 12. The conductive coating 20A can be of a conductive material such as silver-filled ink. A first electrical contact 22A provides a means of connection for the detection of a first signal from the first conductive coating 20A.

On the second side 12B of the piezofilm strip 12 are a plurality of conductive coatings 24A, B and C. Each of the conductive coatings 24 (A–C) lies within the respective sections 18 (A–C) of the piezofilm strip 12, forming the three sensing elements. These conductive coatings collect the charge generated by the piezoelectric film between the coating on opposite sides. No charge is collected from the film that does not have conductive coatings on both sides, thereby providing the means to electrically isolate the charges generated by the 3 sensing elements of the single strip of piezoelectric film from each other. An electrical contact 26 (A–C) is connected to each of the conductive coatings 24 (A–C), and provides an output signal therefrom referenced to the common conductive coating on the opposite side of the film. In the preferred embodiment, the dimensions of conductive coatings 24 (A–C) are as follows: 24B and C are each approximately 4 mm×4 mm and 24A is approximately 4 mm×8 mm. Thus, the area of the conductive coating 24A in the center section 18A is approximately equal to the sum of the areas of conductive coatings 24B and 24C. An insulating layer 28 covers the conductive coatings 24 (A–C).

The support member 14 comprises two rails 14A and 14B. The piezofilm strip 12 is mounted on the supporting member 14 such that rails 14A and 14B support a piezofilm strip 12 at a position between adjacent sections 16A–16B and 16A–16C. The ends of piezofilm strip 12 are attached to each end of support member 14.

In the preferred embodiment, a pneumatically activatable balloon 30 as shown in FIG. 1B is positioned on the other side of support 14. When the balloon 30 is inflated via air tube 32, which is connected to a pressurized air supply at the other end, it causes the support 14 to press and hold piezofilm strip 12 against the tissue.

An additional key feature of the preferred embodiment is that it causes the center element of the sensor, once properly applied to the wrist, to maintain a position approximately centered over the artery.

Figure 2A:
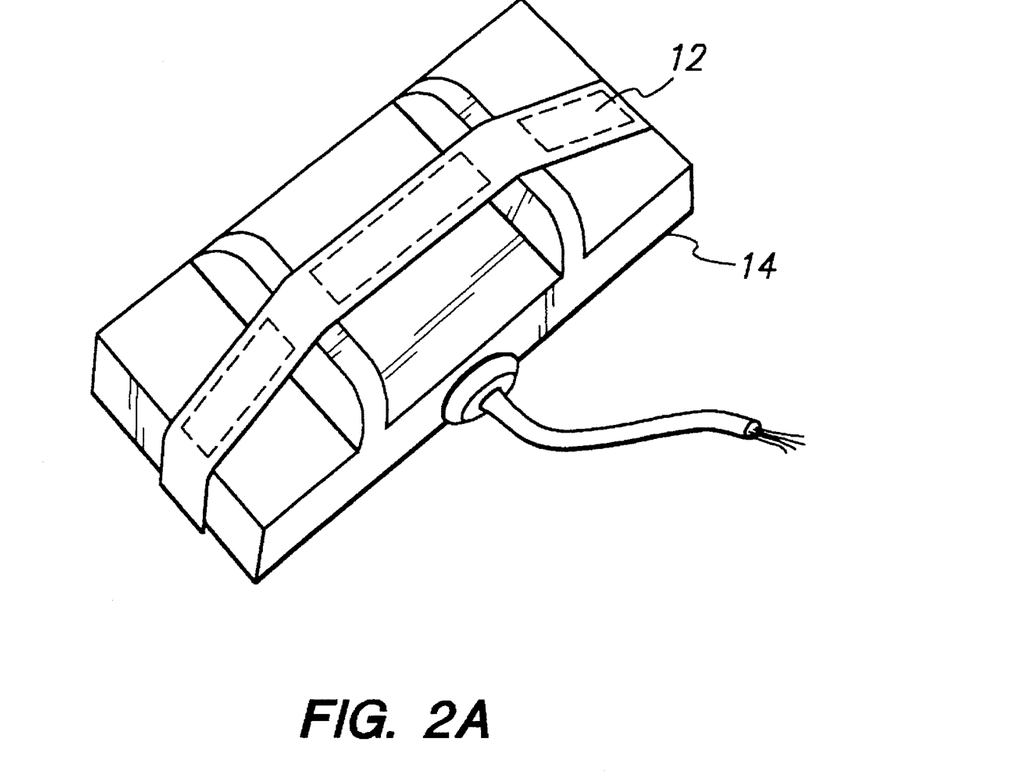
FIG. 2A is an embodiment of the sensor of the present invention with a rigid framework.
Figure 2B:
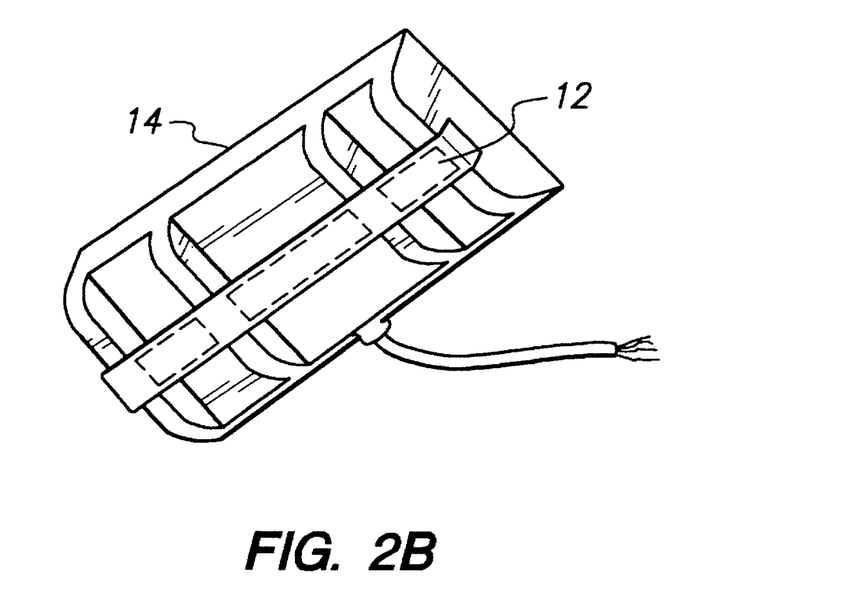
FIG. 2B is an embodiment of the sensor of the present invention with a rigid framework and end rails for defining the contour of the elements in configurations different than in FIG. 2A.

FIG. 2A shows an embodiment of the sensor 10 with a rigid support member. FIG. 2B is an embodiment that also contains a rigid support member on each end, to which the piezofilm is attached, in addition to the rails separating the center and outer channels. The relative height of the outer rails with respect to the inner rails can be used to provide for various sensor contours by varying the angle of the outer elements with respect to the center element.

Figure 3:
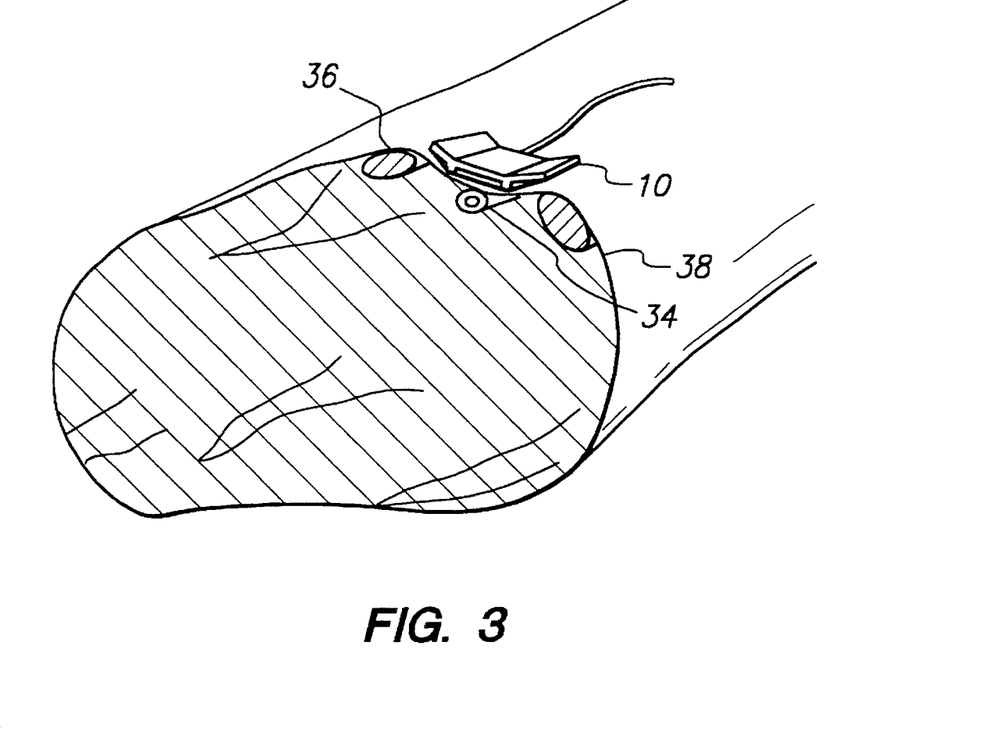
FIG. 3 shows a schematic diagram of the positioning of the sensor of FIG. 1 over a radial artery.

As shown in FIG. 3, radial artery 34 lies between two rigid members in the wrist, tendon 36 located toward the center of the wrist and bone 38 located at the outside (thumbside) of the wrist. The radial artery in humans lies within the channel created by these two members, and is protected by them. The sensor configuration shown in FIG. 1A and its dimensions are designed to allow the center to seat itself within this region. The dimensions are such that the two rails 14A and 14B fit between the tendon and the bone, thereby maintaining the center element over the artery.

Center cavity 16A is placed directly over the artery. The side of the piezofilm strip which comes in contact with the skin is coated with a conductive material 20A and is connected to ground. This is necessary because extraneous electrical signals may be present at the skin's surface and may add noise to the pulse signal. There are also conductive coatings 24 (A–C) that form each of the three positive electrodes on the side of the piezofilm strip facing away from the skin. These conductive coatings collect the charge from each element, and provide means of electrical contact to the amplifier circuitry. Charges will only flow from the portions of the piezofilm strip coated with conductive material on both sides.

A short circuit between the two layers of conductive coating on opposite sides of the piezofilm would eliminate the pulse signal. A short circuit between two conductive coating sections on the same side of the film would reduce the noise-canceling capability of the sensor. Such electrical shorts can be created by moisture on a patient's skin, adhesive material left from certain medical adhesives, and other means. To prevent shorts, the piezofilm is coated with an insulating material 28 over the conductive coatings on the ungrounded side of the sensor. The grounded side is the common electrode side that contacts the skin, and is left uncoated to allow electrical contact and grounding to the patient.

Piezofilm strip center portion 24A senses artifact signals mixed with the arterial pressure wave signal. This artifact signal may be created by muscle movement or other external forces and becomes part of the signal measured by the piezofilm strip and sent as a first output signal to the amplifier circuit. Muscle movement and other sources of artifact are also measured by outer element piezofilm strip portions, but the pressure wave signal is minimal. These signals are sent as a second and third output signal to the amplifier circuit in the preferred embodiment.

Figure 8:
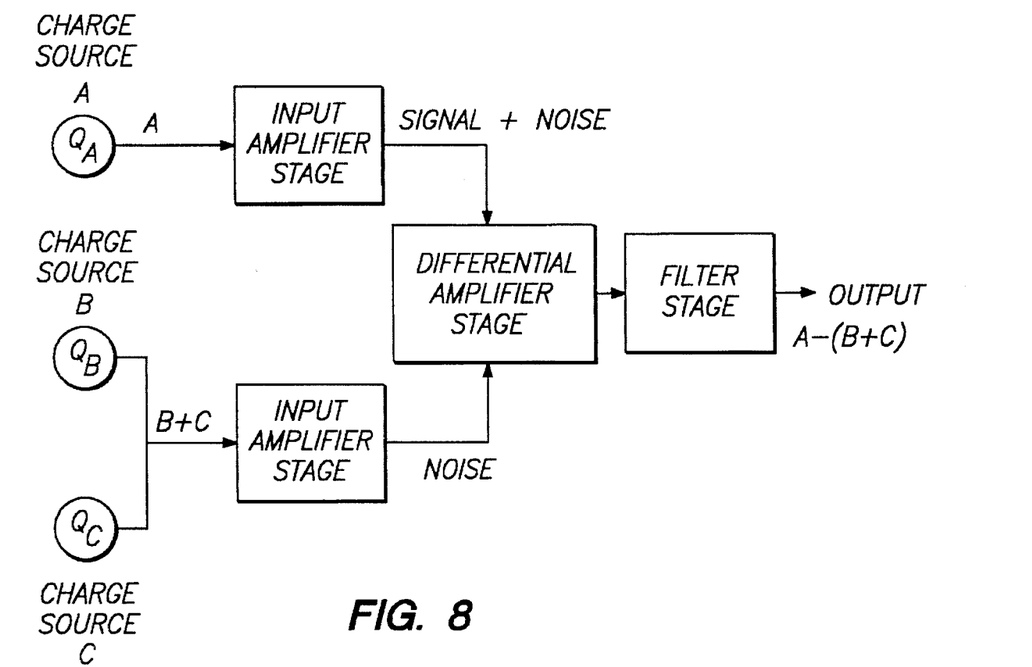
FIG. 8 is a block diagram of the sensor amplifier circuit.

FIG. 8 shows a block diagram of the general operation of the electronic signal processing circuitry. Before describing all of the elements in the circuit shown in FIG. 9 or 10 in detail, a brief description of the general operating method of the pulse sensing device of FIG. 1 may be useful.

The portion of the piezoelectric strip 12 spanning the center channel 16A acts as a charge source when tension is applied to it. The charge source generates a charge proportional to the displacement of the underlying tissue which in turn is a function of the underlying pressure waveform being measured. The charge signal also includes charges resulting from other causes such as movement of the arm to which the pulse sensing device is attached. These signals add artifact to the pressure wave signal. The portions of the piezoelectric strip placed over the two outer channels generate a charge proportional to the artifact just described. In the preferred embodiment, the signals from charge sources 24 (B+C) are amplified and converted to a voltage signal by amplifier stages before being sent to a differential amplifier, where they are subtracted from the signal generated by charge source 24 (A), which is amplified by another amplifier stage. The output from differential amplifier stage may then be sent through a filter stage to filter out unwanted high and low frequencies, with the resulting signal being a waveform that is a function of the pressure waveform inside the artery of the person being measured.

Figure 9:
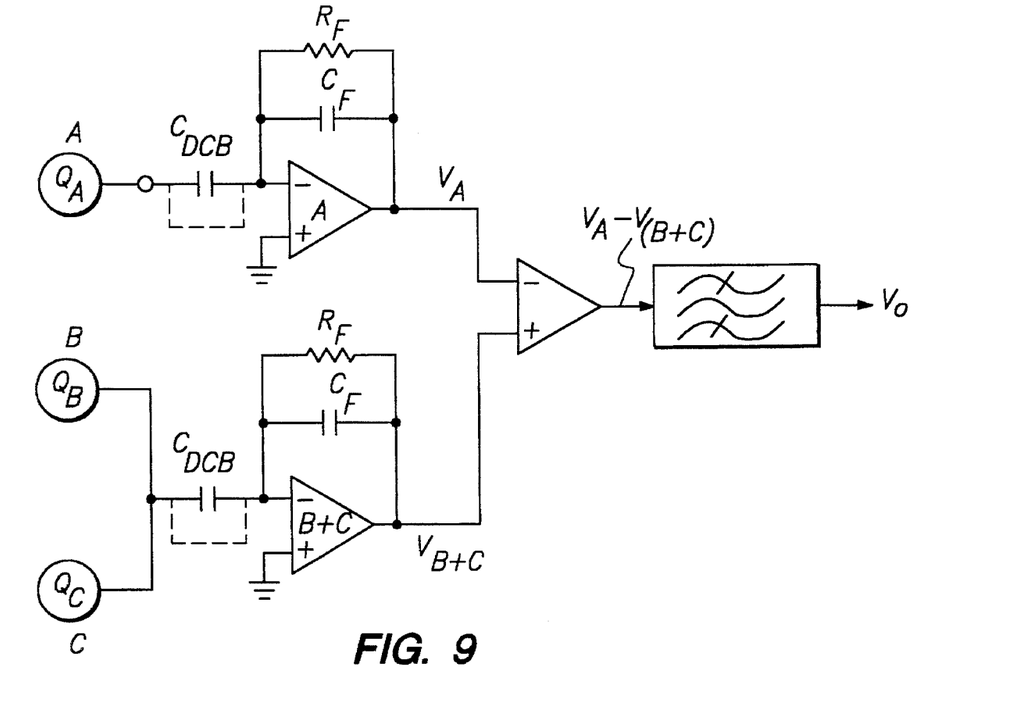
FIGS. 9 and 10 are amplifier circuits for use with the described sensors.
Figure 10:
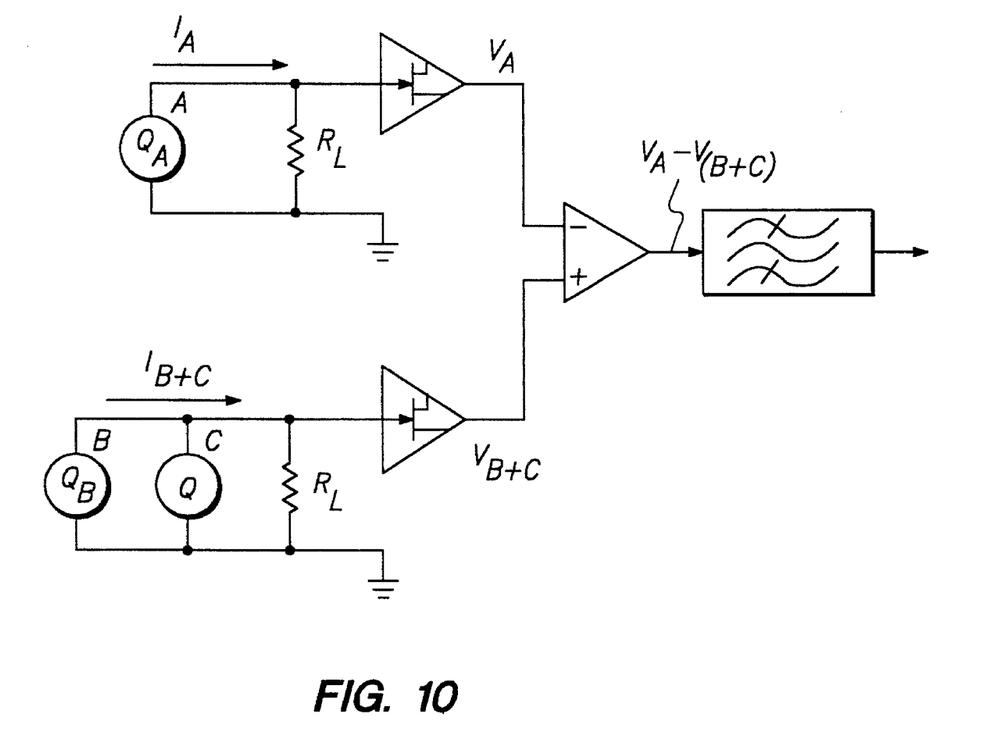

FIGS. 9 and 10 show two versions of amplifier circuit for use with the pulse measuring device as embodied by FIG. 1. In the preferred embodiment of the present invention, the circuit is external to device and may be connected to it as shown in FIG. 1 through collection of wires and connector(s). In an alternate embodiment of the present invention, part of the circuit may be placed on a circuit board that is on the top of support member 14.

The portion of piezofilm strip 12 located over center cavity 16A is represented as charge source QA in FIGS. 9 and 10. The portions to each side are represented as charge sources QB & QC. Charge source QA is connected to the input of preamplifier A. Charge sources QB & QC are connected in parallel to sum the charges, and connected to the input of preamplifier (B+C). Various types of preamplifiers can be used. Two common types of amplifier circuit are shown in FIG. 9 and FIG. 10. The type in FIG. 9 uses an input amplifier commonly known as a charge amplifier. It produces a voltage output proportional to the charge applied to the summing node of the operational amplifier. The charge generated by the piezoelectric film, when connected to the low impedance input of the charge amplifier, is proportional to the change in tension and therefore the change in the forces are measured. This charge needs to be substantially integrated to yield a signal proportional to film tension, which is essentially accomplished by the charge amp. The decay time of the charge and hence the time constant of the circuit is set by the parallel combination of $R_F$ and $C_F$. This RC time constant sets the low-frequency cutoff of its respective sensor element. In the preferred embodiment, the RC time constant is approximately 2 sec. The high frequency cutoff at this point of the circuit is set mainly by the mechanical properties of the sensor. Capacitor $C_I$ is a DC blocking capacitor and is optional. It may be necessary where stray, or parasitic DC or low frequency current sources occur in the film side of the circuit. Its value is selected to be much larger than the sensor element capacitance so not to substantially change the frequency response of the system.

The input amplifier circuit shown in FIG. 10 is a high input impedance amplifier with a low output impedance. It may have a voltage gain (Vout/Vin) of less than one. It will have a current gain (Iout/Iin) of greater than one. A single field-effect transistor (FET) can be used as the front-end amplifier. This type of amplifier is commonly called a buffer. The charge generated by the piezofilm charge source is caused to flow as a current through resistor $R_L$, yielding a voltage drop across it (Vq= Iq $R_L$). This voltage is applied to the input of the buffer. The time constant of the circuit, and hence the low-frequency cutoff, is set by the RC network formed by the combination of the film capacitance and $R_L$. The high frequency response, as before, is mostly a function of the mechanical properties of the sensor.

The outputs of preamplifiers go to a differential amplifier, which subtracts the output of preamplifier (B+C) from the output of preamplifier A. The output of the differential amplifier represents the pulse signal with suppressed or canceled artifact, and is sent to a bandpass filter for attenuation of unwanted high and low frequencies.

Figure 5:
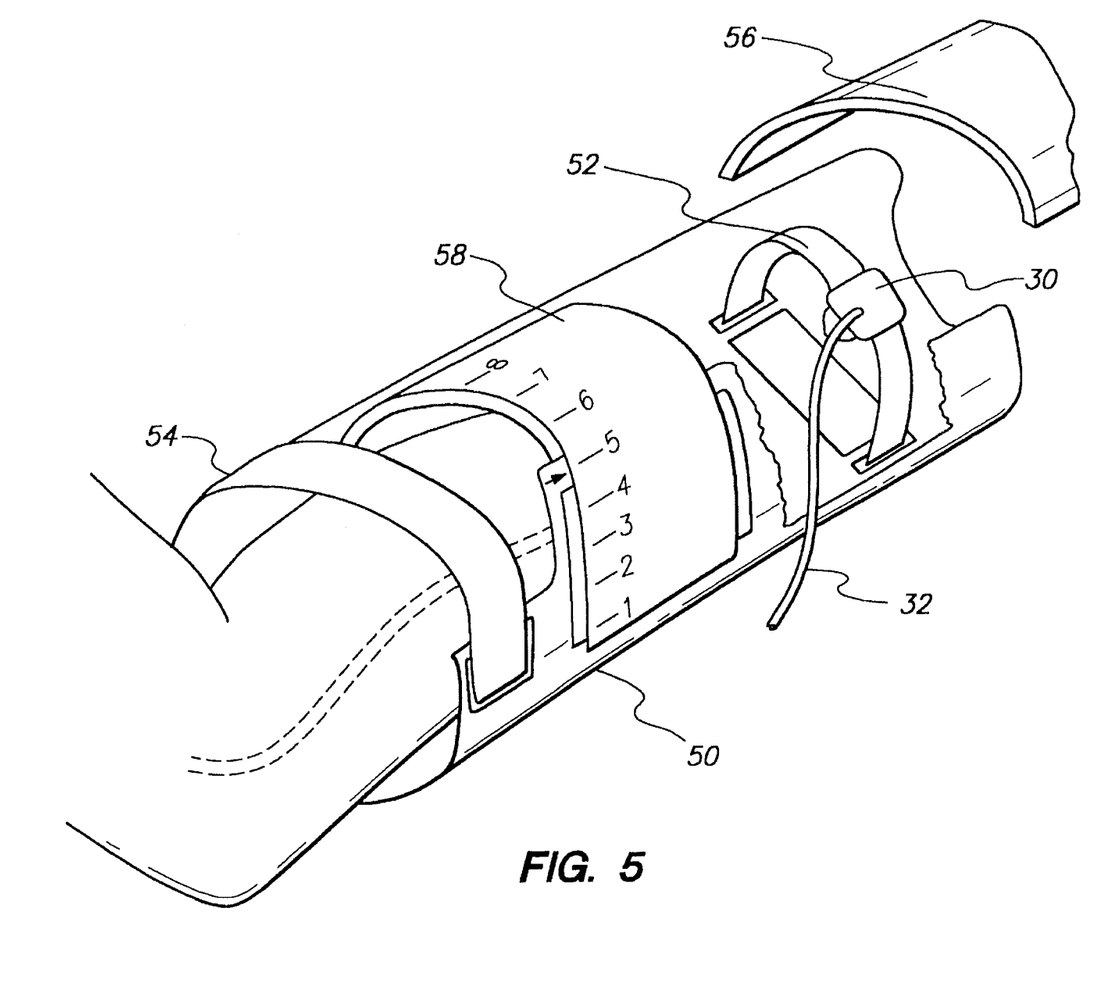
FIG. 5 is a drawing of the wrist stabilizer of the present invention that contains the sensor hold-down air bubble and the cuff assembly for obtaining calibration readings.

FIG. 5 is a drawing of wrist stabilizer 50 containing a hold-down bubble 30, attached to a hold-down strap 52. Wrist stabilizer 50 is designed to maintain a wrist at an angle of flexion that yields a large amplitude of the sensed signal. It is also designed to limit the degree of wrist rotation and finger movement.

Pressurized air is supplied by means of air tube 32 to hold-down bubble 30, and the bubble is inflated after the sensor and bubble are positioned correctly. During this inflation process, the signal from sensor 10 is monitored, and a calculation is made by a separate electronic device to determine the optimum hold-down pressure for each individual.

U.S. Pat. No. 4,799,491 by Eckerle describes a method for determining a hold-down pressure by fitting a polynomial to "a set of at least one of the diastolic pressure, systolic pressure and pulse amplitude versus hold-down pressure values over a range of hold-down pressures between which the underlying artery is unflattened and it is occluded."

The present invention differs from this technique in three very significant ways:

1. As the hold-down pressure is varied from a low to a high value, the waveform from the underlying sensor is analyzed, to determine a range of hold-down pressures over which the morphology of the pressure waveform does not change.

2. Simultaneously, a measure of the signal to noise ratio, as determined by the ratio of the sensor output signal to the noise signal in the outside elements of the sensor (previously described), is determined as a function of hold-down pressure.

3. The hold-down pressures are not selected to provide flattening of the artery.

In one embodiment, the hold-down pressure is determined as the minimum pressure at which the signal waveform maintains its shape (i.e., the morphology of the waveform does not change), and the signal to noise ratio is maximum.

Alternatively, the criteria for determining the hold down pressure may be that pressure which provides the maximum amplitude undistorted signal.

The optimum hold down pressure is then maintained automatically by independent pressure servo means (not shown).

Protective cover 56 is attached to wrist stabilizer 50 over sensor 10 to minimize contact by persons or objects that may cause movement of these items during use, e.g. in an operating room or intensive care unit of a hospital.

Cuff 58 provides means of occluding the radial artery during determination of a calibration or confirmation pressure reading. During the process of deflating cuff 58, sensor 10 of FIG. 1 may be monitored to determine the cuff pressures at which Korotkoff sounds begin and end, in order to determine systolic and diastolic pressures. For decreasing cuff pressure, the Korotkoff sounds begin at the point where cuff pressure is just below the peak intra-arterial pressure (systolic pressure) and end at the point where cuff pressure is just below the minimum intra-arterial pressure (diastolic pressure).

An additional feature of this embodiment as shown in FIG. 5 is the addition of the forearm calibration scale on the cuff. When taking blood pressure with an occlusive cuff, the degree of accuracy obtained is related to the ratio of cuff width to arm circumference. A typical value for this ratio is approximately 0.4. The smaller this ratio becomes, the more the measurement tends to err toward the high pressure side, and vice versa.

The numbers shown printed on the cuff in FIG. 5 provide a means of determining a relative measure of the circumference of the arm around which it is wrapped. For example, if the arrow is pointing at number 2, it indicates a much larger forearm than if it were pointing at number 7.

Various means can be used to utilize this information. In the preferred embodiment, the indicated Arm Circumference Number is manually input to the cuff controller unit, and is then used by the controller unit to apply an appropriate scaling factor to the measurement.

In an alternate embodiment, the cuff bladder can be provided with multiple air chambers, and the Arm Circumference Number can be used to determine the number of chambers to be inflated, so as to maintain the above mentioned ratio near the nominal value.

Means for automatically reading the Arm Circumference Number, such as by photo-electrical means, can be used to automatically determine and input the number to the controller, thereby eliminating the manual step required above.

Incorporating cuff 58 in wrist stabilizer 50 as shown in FIG. 5 provides a convenient means of applying the cuff to the subject's forearm, instead of applying a separate cuff to the subject's upper arm, while providing a means of handling various size arms with a single unit, and also permits using the same sensor to measure the arterial waveform and the Korotkoff sounds. Strap 54 provides a means of holding wrist stabilizer to subject's forearm.

Figure 4:
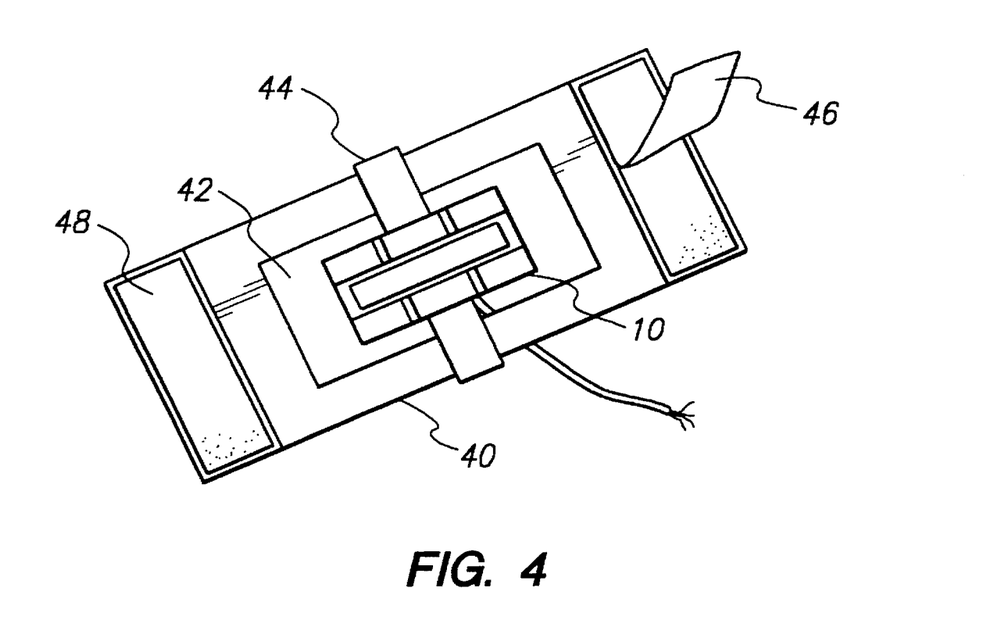
FIG. 4 is a diagram showing the apparatus of FIG. 1A mounted to an adhesive strip that permits attachment to the skin and repositioning of the sensor.

FIG. 4 shows a sensor 10 attached to adhesive backed strip 40 by means of plastic slide tabs 44. Strip 40 has a rectangular section 42 cut out of its center to allow mounting sensor 10, so as to permit sensor 10 to be moved after the adhesive strip has been attached over an artery and before the hold-down bubble is inflated. End cover strips 46 are removed prior to application to expose adhesive 48 on each end of the strip. Thus, once the tape has been applied to the subjects arm, the sensor 10 can be more accurately positioned, or repositioned in the event it is inadvertently moved from the appropriate site.

Figure 12:
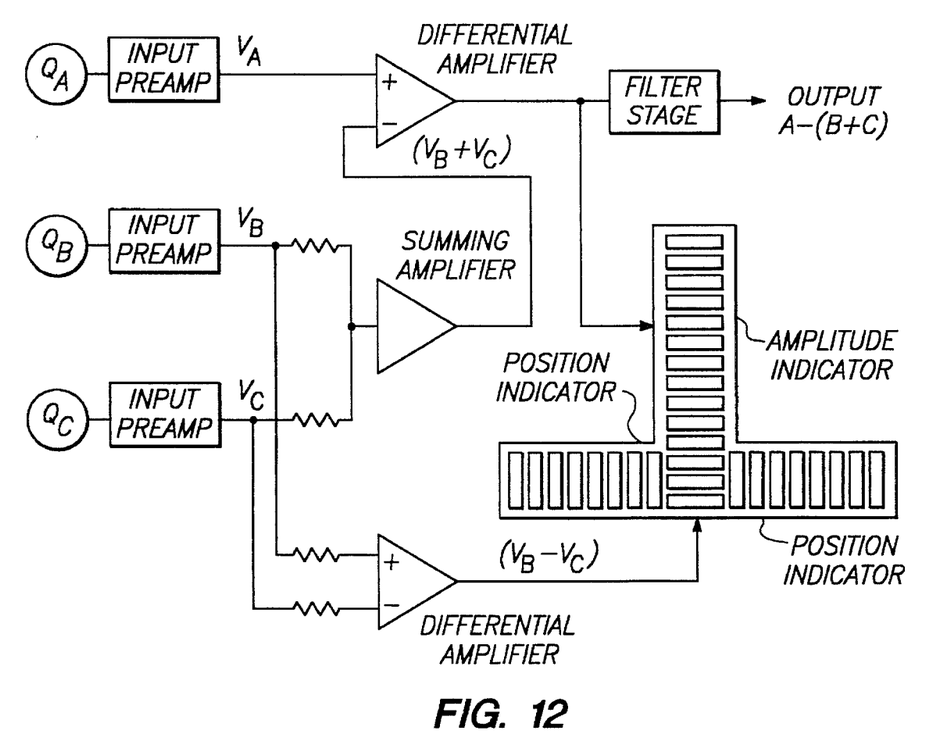
FIG. 12 shows an embodiment of the present invention whereby the charges produced by separate segments of the sensor are input to separate preamplifiers.

As previously mentioned, it is important to properly position the sensor, and to maintain this position. FIG. 12 shows an embodiment whereby the sensor segments (FIG. 1E-24A, 24B, 24C) are brought out separately. Each segment is connected to its own separate preamp, producing voltage signals $V_A$, $V_B$, $V_C$. Signals $V_B$ and $V_C$ are summed via a summing amplifier and produce a signal $(V_B+V_C)$ which is then subtracted from $V_A$ to produce the A-(B+C) signal as shown in FIG. 8. It is also applied to a Verticle Bar Graph display. Signals $V_B$ and $V_C$ are also subtracted and create signal $(V_B-V_C)$. This is the position signal, and is a measure of how close the artery is to each of the side segments. Signal $(V_B-V_C)$ is positive when the artery is near 24B (FIG. 1E)w, negative when near 24C, and zero when equally distant to each. This signal is applied to the horizontal bar graph in FIG. 12. The inverted "T" shape helps the visual interpretation of the two graphs.

Figure 6:
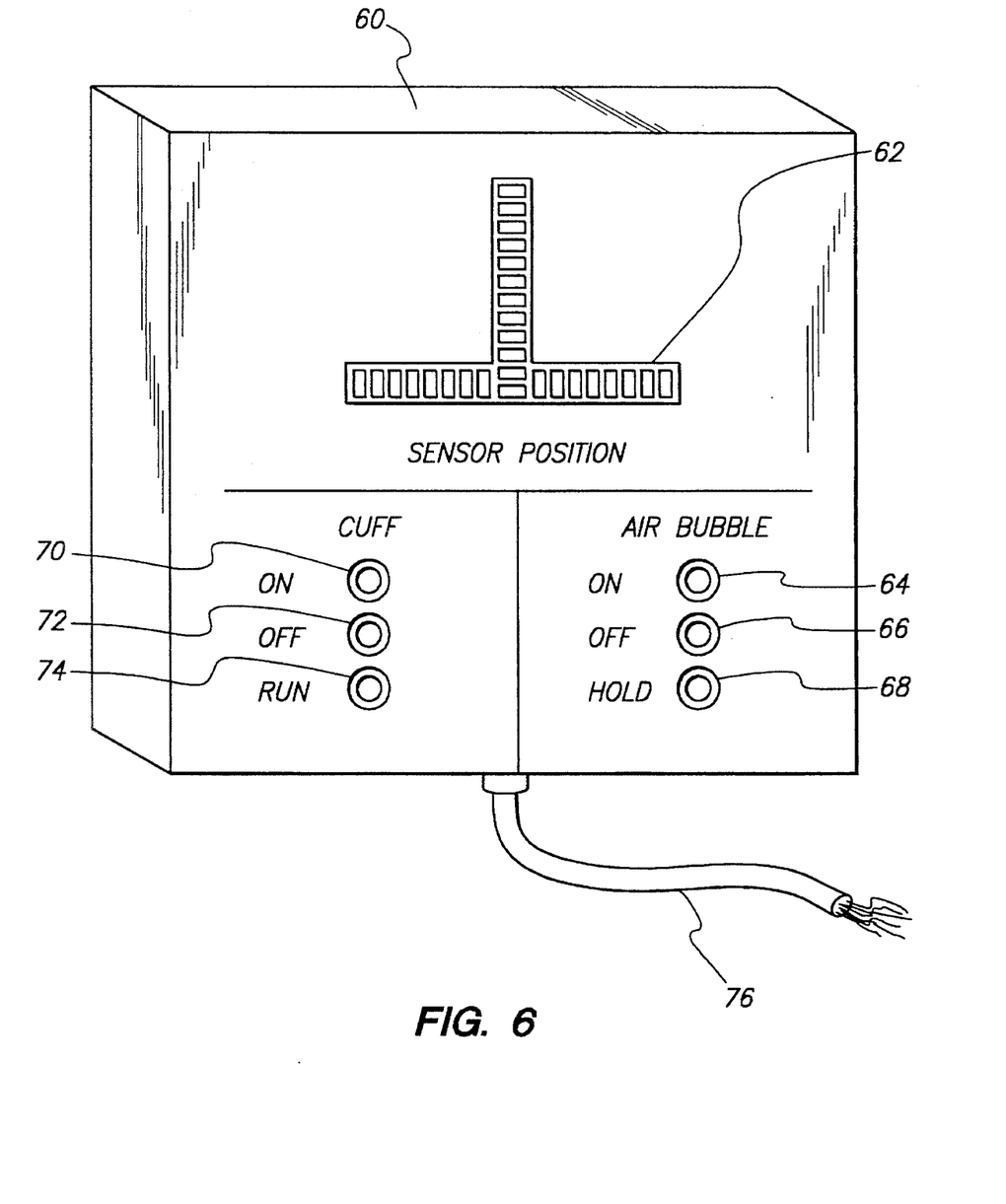
FIG. 6 is a drawing of the position indicator with air bubble and cuff inflate/deflate controls.

FIG. 6 shows small electronics module 60 with visual indicators 62, such as LED or LCD devices. The center vertical column of indicators are lit in a pulsating manner corresponding to the sensed pressure pulse when the center element 24A of sensor 10 is properly positioned over the artery, with the maximum number of indicators lit indicative of the amplitude of the signal from the center element 24A.

If the sensor is positioned too far to one side of the artery, e.g., too far to the left, the right horizontal row of indicators will pulsate, indicating that the sensor should be moved to the right, and similarly if too far to the right, the left horizontal row of indicators will pulsate.

Control button 64 is used to initiate determination of the appropriate hold-down pressure as previously described. Control button 66 is used if it is desired to remove the pressure from the hold-down bubble 30, for example, in the event the sensor must be repositioned, or the monitoring process is to be terminated.

Control button 70 is used to initiate a calibration reading utilizing cuff 58 and sensor 10, and button 72 may be used to terminate a calibration reading. Electrical cable 76 provides electrical connection of module 60 to a separate control device.

Figure 7A:
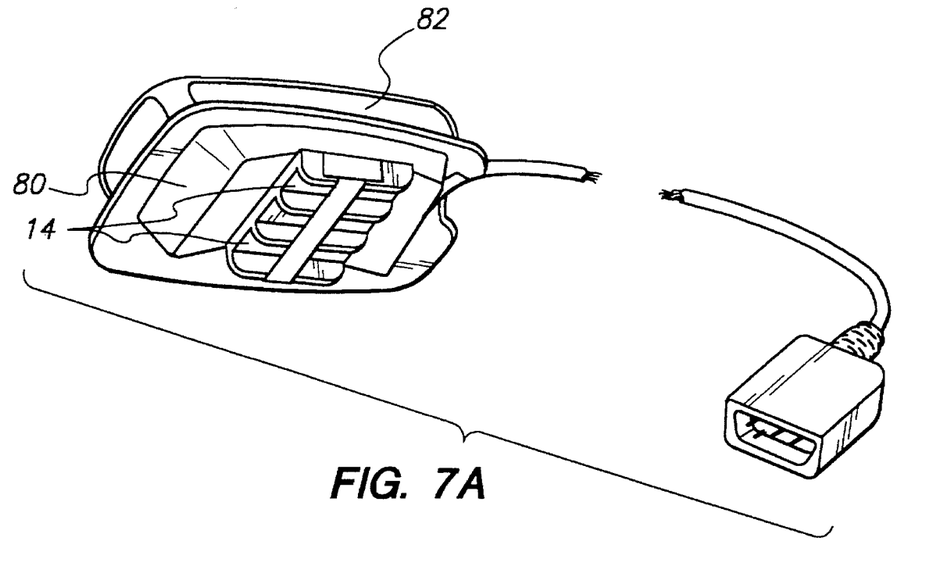
FIG. 7A is a perspective view of the sensor of the present invention with an alternate hold-down means.
Figure 7B:
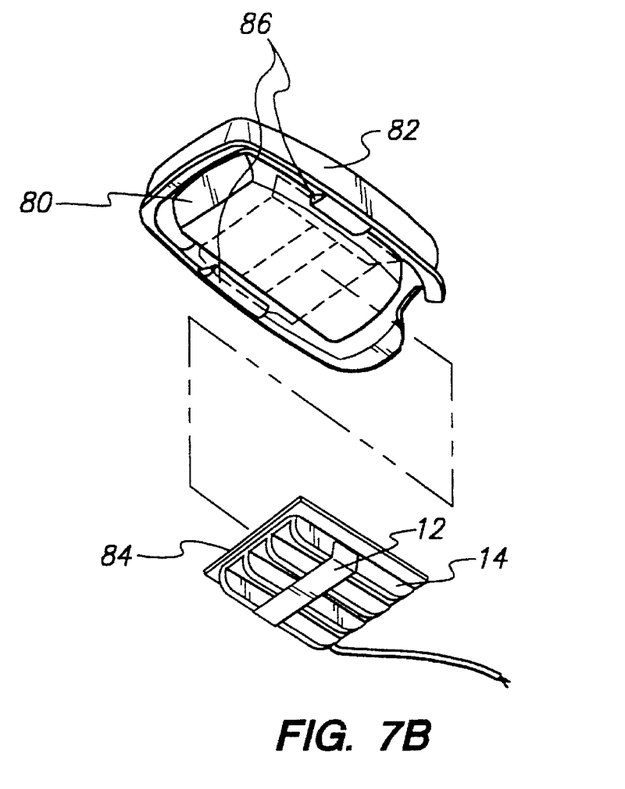
FIG. 7B is an embodiment of the sensor assembly shown in FIG. 7A, wherein the sensor portion is disposable.

Another embodiment to hold the Sensor 10 in its position with appropriate force is shown in FIG. 7A and 7B. FIG. 7 shows two versions of the differential sensor that permit it to be applied over an artery, using a resilient material such as a foam rubber member between the sensor body and an outer shell held to the body, as the hold-down mechanism. An example of such an artery could be the Dorsalis Pedis artery in the foot. This version of the sensor is protected by a "turtle shell" housing, which may be attached to the skin using adhesive tape, hold down bubble as previously described, or other suitable means. The pressure with which the sensor is held on the skin over the artery is determined by the resilient material inside the housing.

In the embodiment of FIG. 7, support member 14 is attached to resilient material 80. The resilient material 80 typically has enough resiliency to keep the pressure the piezofilm strip exerts on the skin between 0.5 to 0.8 pounds per square inch (psi). If pressure exerted by the piezofilm strip is below 0.5 psi the piezofilm may not be able to accurately measure the displacement signal, while if pressure is above 0.8 psi the artery may be constricted, which results in a distorted waveform. In one embodiment, resilient material 80 is a piece of foam. The resilient material 80 is then enclosed in an outer shell 82. Outer shell 82 is made of a hard, rigid material to limit external sources of artifact. If outer shell 82 is tapped, bumped, or otherwise disturbed while the pulse is being measured, most of the stress on the system will be distributed along the shell's edges to the arm or other body surface rather than directly to support member 14.

Sensor of FIG. 7A is intended to be disposable, and thus is made of inexpensive materials with minimal electronics in the actual sensor. Various other embodiments of the present invention are described below, but in no way is the present invention limited to just these embodiments. Another disposable version of the present invention is shown in FIG. 7B. In this disposable version, sensor 10 contains a removable portion 84 comprising support member 14 and piezoelectric strip 12. Removable portion 84 is inserted into frame structure 86 attached to resilient material 80. Disposable member 84 can be attached to frame 86 in a variety of manners. One embodiment of the present invention has disposable member 84 sliding into and out of frame 86. Electrical contacts on the inside of frame 86 connect to contacts on the surfaces or edges of member 84. Members 84 and 14 may be one unit. A disposable pulse wave measuring device can be very advantageous because of medically related concerns of cleanliness and sanitation. After each use, disposable member 84 is replaced by a new, identical disposable member. This allows more expensive materials to be used for the resilient material, and also allows more electronics to be used economically in the nondisposable portion of the sensor if required.

The preferred embodiment discloses a pulse sensing device which utilizes three channels and therefore three distinct portions of piezoelectric material. Three portions of piezoelectric material are used so that one portion measures the pulse signal and the two adjacent portions measure artifact on each side of the center portion. However, many different arrangements of the piezoelectric material can be used to detect the pulse signal and unwanted artifact. The number of distinct portions of piezoelectric material can be varied. At least two portions are required so that separate signals can be detected for the pulse and artifact. The only difference in a pulse measuring device utilizing a larger number of piezoelectric portions is that the signal from multiple portions of piezoelectric material must be combined to determine the pulse signal and/or artifact signal.

The preferred embodiment described above uses one piezoelectric strip covered with a conductive material having a specified surface area to measure the pulse signal. The size of the signal is proportional to the area of piezofilm over which the electrical contacts extend on both sides of the film.

In that embodiment, the combined surface area of the conductive material on the two piezoelectric strips which measure mainly artifact is equal to the surface area of the conductive material on the piezoelectric strip that measures mainly pulse. This is done to ensure that the artifact signal detected along with the pulse signal is accurately canceled by the signal from just the artifact detectors. However, other embodiments of the invention may not use sensor elements that employ equivalent active surface areas to ensure that the correct motion artifact signal is subtracted from the pulse signal. These embodiments could vary the relative amplification of the different element signals to accomplish the same ends.

Other embodiments of the present invention do not amplify either the pulse signal or motion artifact signal before the cancellation process. To ensure that signal strength is strong and accurate enough in these embodiments, either the entire calculating means is placed on circuit board or collection of wires carrying signals to the calculating means is shielded to prevent extraneous noise being added to either signal.

Figure 11:
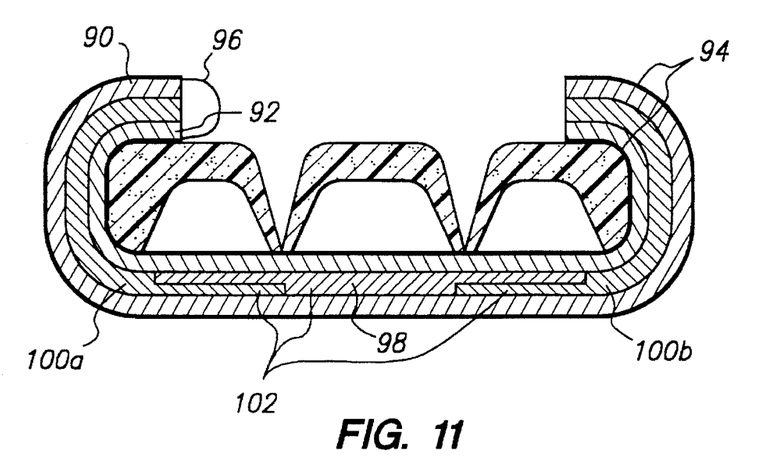
FIG. 11 shows the piezoelectric film assembly for an embodiment of the sensor that directly provides a noise-canceling signal from the sensor.

An alternate embodiment accomplishes the subtraction within the sensor of the signals from the side noise-pickup elements from the signal of the center element without additional electronics. As shown in FIG. 11 two strips of piezoelectric film, 90 and 92, are in close proximity to each other in a similar physical orientation to form a sandwich-like structure. This structure takes the place of the single strip of piezoelectric film in the various embodiments. The electrical polarity of the two films are oriented with a positive side of one film and a negative side of the other film on the inside of the sandwich-like structure. The outer sides of the film, which are the outside surfaces of the sandwich-like structure, are conductively coated with, e.g., silver filled ink 94, and these coatings form one electrode of each of the sensing elements. The coatings on each strip are electrically connected together by an electrical connection 96, and together form the common electrode and a sensor output electrical connection. One piezoelectric strip has a conductive coating 98 on its inside surface, which is on the inside of the sandwich-like structure, in the center region of the strip. This coating acts as a second electrode of the center element, and defines its active area. The other piezoelectric strip has two conductive coatings 100 $a$ & $b$, on its inside surface, which are located toward the ends of the strip, to form second electrodes of the side noise-sensing elements, and define their active areas. A small portion of each of these 2 coatings, which are toward the center of the strip, overlap and are physically, and thereby electrically, in contact with the inside coating on the other piezoelectric strip. The electrical connections made between these conductive coatings (100$a$, 98, and 100$b$) on the inside surfaces of the strips effectively perform the subtraction of the charge signals of the side elements from the signal of the center element, due to the reverse polarity of the piezoelectric film with respect to these inner conductive coatings. A force applied to a surface of the sandwich-like structure produces a certain charge in the center element, and charges of opposite polarity in the side elements. The sizes of the inner coatings are made to define active areas of the elements such that the total active area of the side elements is substantially equivalent to that of the center element, thereby yielding a noise-canceling sensor that generates substantially no total charge output from the sensor when the same forces are applied to each of the sensing elements of the structure. An insulating material is placed or applied within the sandwich-like structure between the inner conductive coatings on the strips, and the uncoated surface of the other strip. This prevents each inner electrode from conducting charge of the opposite polarity from the other film. The inner electrodes can be applied to leave narrow regions along the edges of the film uncoated, and insulating material can be placed in these regions to prevent shorting of the electrodes of the elements from moisture or contaminants. A sensor signal is obtained from the electrically connected outer electrodes forming the common electrode, and the electrically-connected inner electrodes of the 3 sensing elements, thereby producing a single noise-canceled signal without using other electronic means. This signal can then be amplified by a charge amplifier or buffer as previously described.

Other embodiments can use other sensing materials or elements in place of the piezoelectric film in various embodiments. Such materials or elements include, but are not limited to, piezoresistive and magnetostrictive materials, other piezoelectric materials or elements, optical or magnetic sensing devices, or other devices that may become available in the future.

Having fully described one embodiment of the present invention and several alternatives to that embodiment, many other equivalent or alternative methods of sensing an arterial pulse waveform will be apparent to those skilled in the art. These equivalents and alternatives are intended to be included within the scope of the present invention.

What is claimed is:

1. An arterial sensor for measuring the surface force/displacement resulting from a blood pressure wave traveling through an artery and transmitted through the arterial wall and overlying tissue, comprising:

a first piezoelectric sensor for generating a first signal;

a second piezoelectric sensor for generating a second signal;

a support for independently supporting said first piezoelectric sensor and said second piezoelectric sensor; and means for differentially combining said first signal and said second signal;

wherein said first piezoelectric sensor comprises a common piezoelectric strip having a common electrical contact and a first piezoelectric strip having a first electrical contact, and said second piezoelectric sensor comprises a second piezoelectric strip having a second electrical contact;

wherein said first piezoelectric strip has an area less than that of said common piezoelectric strip and said second piezoelectric strip has an area less than that of said common piezoelectric strip.

2. The arterial sensor of claim 1 wherein said second piezoelectric sensor further comprises said common piezoelectric strip having said common electrical contact.

3. The arterial sensor of claim 2 further comprising:

a third piezoelectric sensor for generating a third signal;

wherein said support is further for independently supporting said third piezoelectric sensor;

wherein said means for differentially combining is further for combining said third signal;

wherein said third piezoelectric sensor comprises a third piezoelectric strip having a third electrical contact;

wherein said third piezoelectric strip has an area less than that of said common piezoelectric strip; and wherein said third piezoelectric sensor further comprises said common piezoelectric strip having said common electrical contact.

4. The arterial sensor of claim 3 wherein said support has three contiguous, adjacent cavities with said first piezoelectric strip in one cavity, said second piezoelectric strip in the middle cavity, and said third piezoelectric strip in the third cavity.

5. The arterial sensor of claim 4 wherein said second piezoelectric strip measures the force/displacement resulting from said blood pressure wave travelling though said artery, and said first piezoelectric strip and said third piezoelectric strip measure noise artifact.

6. The arterial sensor of claim 5 wherein the area of said second piezoelectric strip is substantially equal to the sum of the areas of said first and third piezoelectric strips.

7. The arterial sensor of claim 6 wherein said first differential combining means subtracts said first and third signals from said second signal.

8. The arterial sensor of claim 6 further comprising a second differential combining means for subtracting said first signal from said third signal.

9. The arterial sensor of claim 8 further comprising a visual indication of magnitude and polarity of the output of said second differential combining means.

10. The arterial sensor of claim 5 wherein said means for differentially combining adjusts said first signal by a first factor determined by the relative area of said piezoelectric strips and adjusts said second signal by a second factor determined by the relative areas of said piezoelectric strips.

11. The arterial sensor of claim 1 further comprising:

pneumatically activatable means for engaging said sensor with said artery wherein said blood pressure waveform is detected by said sensor means.

12. The arterial sensor of claim 1, further comprising:

a third piezoelectric sensor for generating a third signal; and wherein said support is further for independently supporting said third piezoelectric sensor;

wherein said means for differentially combining is further for combining said third signal;

wherein said third piezoelectric sensor comprises a third piezoelectric strip having a third electrical contact; and wherein said third piezoelectric strip has an area less than that of said common piezoelectric strip.

13. An arterial sensor for measuring the surface force/displacement resulting from a blood pressure wave traveling through an artery and transmitted through the arterial wall and overlying tissue, comprising:

a first piezoelectric sensor for generating a first signal;

a second piezoelectric sensor for generating a second signal;

a support for independently supporting said first piezoelectric sensor and said second piezoelectric sensor; and means for differentially combining said first signal and said second signal;

wherein said first piezoelectric sensor comprises a first piezoelectric strip having a positive side and a negative side;

wherein said second piezoelectric sensor comprises a second piezoelectric strip having a positive side and a negative side; and wherein said positive side of said first piezoelectric strip is electrically connected to said negative side of said second piezoelectric strip.

14. The arterial sensor of claim 13 wherein said negative side of said first piezoelectric strip is juxtaposed to, and in physical contact with, said positive side of said second piezoelectric strip to form an electrical connection.

15. The arterial sensor of claim 14 where in a portion of said first piezoelectric strip is conductively coated to form a first electrode and spaced-apart portions of said second piezoelectric strip are conductively coated to form a second electrode and said first and second piezoelectric strips are positioned such that said second electrode is in physical contact with said first electrode.

16. The arterial sensor of claim 13 further comprising:

pneumatically activatable means for engaging said sensor with said artery wherein said blood pressure waveform is detected by said sensor means.

17. The arterial sensor of claim 13, further comprising:

a third piezoelectric sensor for generating a third signal; and wherein said support is further for independently supporting said third piezoelectric sensor;

wherein said means for differentially combining is further for combining said third signal; and wherein said third piezoelectric sensor comprises a third piezoelectric strip having a positive side and a negative side.

18. An arterial sensor for measuring the surface force/displacement resulting from a blood pressure wave traveling through an artery and transmitted through the arterial wall and overlying tissue, comprising:

a strip of non-conductive material having a first side and a second side;

a first conductive film on said first side;

a plurality of spaced apart second conductive films on said second side, each of said second conductive films having an area less than that of said non-conductive material;

a plurality of electrical contacts one to each of said first conductive film and each of said plurality of second conductive films; and a support for independently supporting said plurality of spaced apart second conductive films.

19. The arterial sensor of claim 18 wherein said conductive film is a piezoelectric film.

20. The arterial sensor of claim 18 wherein said plurality of spaced apart second conductive films includes three spaced apart conductive films.

21. The arterial sensor of claim 18 wherein said sensor generates a plurality of signals, one signal from each of said electrical contacts.

22. The arterial sensor of claim 21 further comprising means for differentially combining said plurality of signals.

* * * * *